US00PP34223P2

(12) United States Plant Patent
Hansen

(10) Patent No.: US PP34,223 P2
(45) Date of Patent: May 10, 2022

(54) ***PHLOX* PLANT NAMED 'RUBY RIOT'**

(50) Latin Name: ***Phlox* hybrid**
Varietal Denomination: Ruby Riot

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,227

(22) Filed: Nov. 19, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

(56) References Cited

U.S. PATENT DOCUMENTS

PP31,485 P2 * 2/2020 Hansen ..... A01H 6/70
Plt./320

OTHER PUBLICATIONS

North Branch Nursery, Inc. Perennial Inventory Sep. 16, 2020, retrieved on Mar. 3, 2021, retrieved from the Internet at http://www.northbranchnursery.com/wp-content/uploads/perennial.pdf, pp. 1 and 31. (Year: 2020).*

* cited by examiner

*Primary Examiner* — June Hwu

(57) ABSTRACT

A unique cultivar of Hybrid Creeping *Phlox* named 'Ruby Riot' characterized by vigorous, dense, spreading, multi-stemmed, winter-hardy habit with short, bright-green, shiny, linear leaves. Flowering begins in late-April and continuing for up to five weeks in cooler weather conditions, on heavily-branched peduncles and completely cover the plant in peak season. Petals are reddish-purple to purplish-red with darker eye marks and a small notch and the tips of the petals. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Ruby Riot'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Dec. 1, 2019. Subsequently, the new plant was advertised in the "Walters Gardens 20-21 Catalog" by Walters Gardens, Inc. released on May 20, 2020. The claimed plant was first sold to Pleasant View Gardens/Proven Winners® on Jun. 15, 2020 by Walters Gardens, Inc., who obtained the plant and all information relating thereto, from the inventor. No plants of *Phlox* 'Ruby Riot' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant known as *Phlox* 'Ruby Riot' and will be referred to hereafter by its cultivar name, 'Ruby Riot', or the "new plant". The new plant was hybridized by the inventor at a wholesale perennial nursery in Zeeland, Mich. on Mar. 24, 2015 as a cross between *Phlox nivalis* var. *hentzii* 'Caswell Pink Eye' (not patented) as the female or seed parent and the proprietary, unreleased, hybrid known by the breeder code 14-308-1 (not patented) as the male or pollen parent. The new plant passed initial evaluation on the spring of 2017 and was assigned the breeder code 15-52-1 through the remaining evaluation process. 'Ruby Riot' was first asexually propagated by stem cuttings in the greenhouses at the same nursery in Zeeland, Mich. in the summer of 2017. The unique characteristics of the new plant have been found to be reproducible and stable in successive generations of asexually propagated plants, and the resultant plants have been found to be identical to the original selection.

BRIEF SUMMARY OF THE PLANT

*Phlox* 'Ruby Riot' is unique from all other Hybrid Creeping *Phlox* known to the inventor. The nearest comparison plants known to the inventor include: the female and male parents, 'Rose Quartz' copending U.S. Plant patent application Ser. No. 16/974,228, 'Rocky Road Pink' U.S. Plant Pat. No. 31,486, 'Red Wing' (not patented) and 'Rocky Road Magenta' U.S. Plant Pat. No. 31,485. The female parent, 'Caswell Pink Eye', has lighter pink flowers. The male parent has flowers that are more purplish-pink on slightly taller plants. 'Rose Quartz' has a similar habit with larger flowers of rose pink. 'Rocky Road Pink' has a smaller habit with slower spreading growth rate and the flowers are bright rose pink. 'Red Wing' has a wider more vigorous growth habit, and the flowers have narrower petals. 'Rocky Road Magenta' has a smaller habit with slower spreading growth rate and vibrant magenta-purple flowers with small dark-purple eye marking and a small notched petal apex.

*Phlox* 'Ruby Riot' differs from all other *Phlox* known to the inventor in the following repeatedly observed traits in combination:

1. Vigorous plants of dense spreading habit, spreading by rooting stems, producing short, clean, puberulent, bright-green, shiny, linear leaves;
2. Multiple heavily-branched stems produce branched panicles;
3. Flower beginning in late-April and continuing for up to five weeks, in cool conditions, completely covering plant at peak flowering;
4. Flowers of reddish-purple to purplish-red with darker eye and with small notches at the tip of the petals;
5. Plant is able to withstand dry conditions once established.

BRIEF DESCRIPTION OF THE DRAWINGS

The photographs of the new plant demonstrate the unique traits of *Phlox* 'Ruby Riot' and the overall appearance of the plant at two-years-old growing in a full-sun trial garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
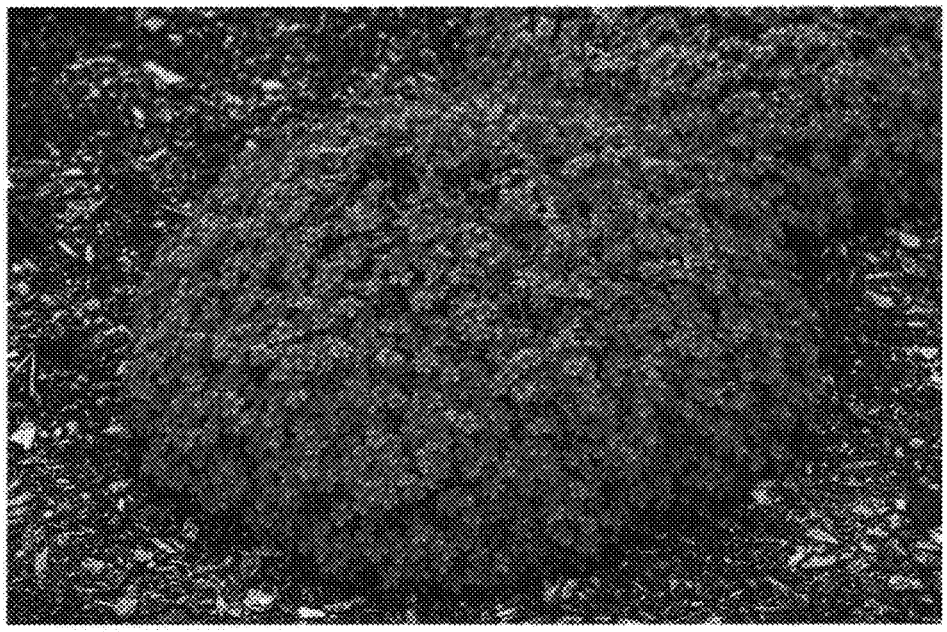
FIG. 1 shows a landscape habit view of the new plant in peak flower.
Figure 2:
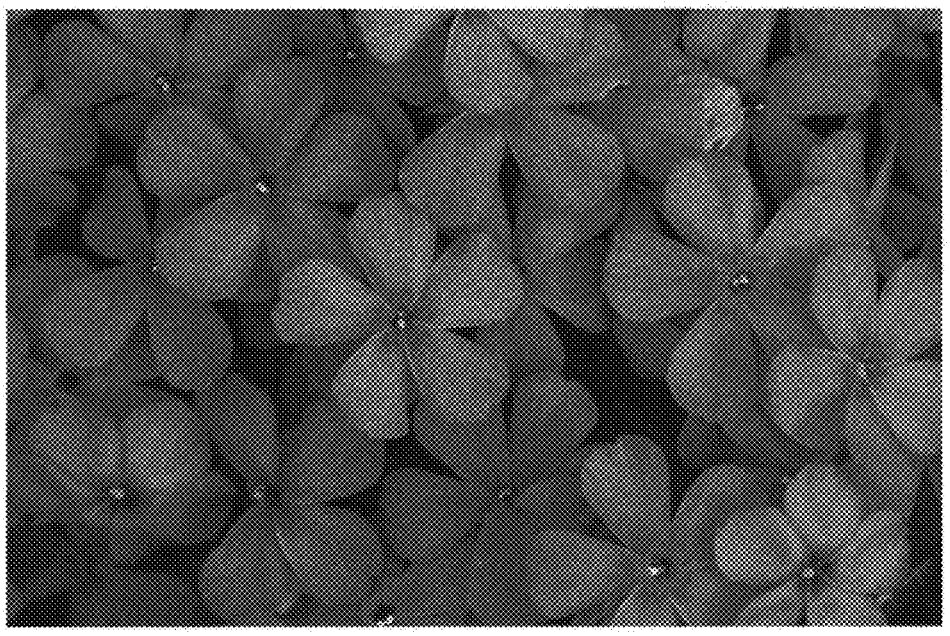
FIG. 2 shows a close-up of the flowers.

The following descriptions and color references are based on the 2015 edition of The Royal Horticultural Society Colour Chart except where common dictionary terms are used. *Phlox* 'Ruby Riot' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox* hybrid;

Parentage: Female or seed parent is 'Caswell Pink Eye', male or pollen parent is the proprietary hybrid known by the breeder code 14-308-1 (14-308-1 is a hybrid between *Phlox subulata* 'Apple Blossom' (not patented) times a proprietary selection of *Phlox* x *procumbens;*

Plant habit: Winter-hardy, evergreen herbaceous perennial; short, dense, producing about 50 stiff, highly-branched prostrate stems; foliage 16.0 cm tall and 42.0 cm wide; flowering to 19.0 cm tall and 46.0 cm wide;

Propagation: Stem cuttings; rooting in about 2 weeks;

Time to produce finished crop in 3.8 liter pots: About 10 to 12 weeks; vigorous;

Root: Fibrous and freely branching; color creamy white to tan depending on soil type;

Leaves: Simple; opposite proximally, whorled distally; linear to subulate; apex narrowly acute to apiculate; base truncate, clasping; margin ciliolate; glabrescent and moderately lustrous both adaxial and abaxial; to about 14.0 mm long by about 2.5 mm wide and 0.7 mm thick at base, average about 12.5 mm long and 2.0 mm wide and 0.5 mm thick at base;

Leaf color: Adaxial expanding nearest RHS 137A and mature adaxial between RHS NN137A and RHS 139A, abaxial expanding nearest RHS 146B and mature nearest RHS 137A; winter adaxial color variable, between nearest RHS 137B in regions protected from sun to RHS 137A with strong blush to nearly solid RHS 187A in high light exposure regions; winter abaxial color variable, between nearest RHS 146A in regions of sun protection, to high sun exposure areas of nearest RHS 146A with moderate blush of nearest RHS 187A;

Foliage fragrance: None detected;

Veins: Pinnate; not conspicuous adaxial and abaxial;

Vein color: Same color as surrounding leaf;

Petiole: Leaves sessile;

Stems: Cylindrical; flexible; wiry; prostrate; puberulent when expanding, highly branching; to about 18.0 mm long and 2.0 mm diameter near base;

Stem color: Young expanding stems nearest RHS 145B, older proximal stems nearest RHS 156A;

Nodes: About 4.0 mm apart proximally; distally less than 1.0 mm apart;

Node color: Color nearest RHS 156A;

Inflorescence: Upright to outwardly; about 2.5 cm long and 4.8 cm wide; average of 3.3 flowers;

Flowers: Perfect; salverform; mostly flat faced; about 24.0 mm across face and 15.0 mm long; with fused corolla tube about 12.0 mm long and 2.0 mm diameter near face; aspect upright to outwardly;

Flower longevity: About 5 days on plant; self-cleaning;

Flower fragrance: Lightly sweet;

Buds one to two days prior to opening: Narrowly oblanceolate, to narrowly clavate; bluntly acute apex with rounded base; petals implicate; about 17.0 mm long, 7.0 mm long in terminal bulb portion and 10.0 mm long in tube; corolla tube to 2.0 mm diameter, bulb to 3.5 mm diameter;

Bud color: Exposed petal bulb portion nearest RHS 85D; between tube and bulb nearest RHS 146B, corolla tube basal 1.0 mm nearest RHS 145C and distal tube nearest RHS 155A; calyx nearest RHS 138A;

Petals: Five; consisting of an obovate limb and basal claw fused into corolla tube; apex rounded, erose and sharply and shallowly cleft to about 1.0 mm deep; limbs not imbricate; margin entire; glabrous adaxial and abaxial;

Petal size: Limb about 10.0 mm long and 9.0 mm wide near middle; tube about 12.0 mm long and 2.0 mm diameter;

Petal color upon first opening:

*Adaxial.*—Limb between RHS 72B and RHS NN78B with two bars about 1.0 mm long and 0.5 mm wide in center eye nearest RHS 79A and central eye between the bars and corolla tube about 1.0 mm wide nearest RHS 76B; proximal 2.0 mm of tube nearest RHS 145C, remaining distal tube portion nearest RHS N75D.

*Abaxial.*—Limb between RHS 72B and RHS N78B with area around inside eye nearest RHS 76D, proximal 2.0 mm of tube nearest RHS 145C, remaining distal tube portion nearest RHS N75B.

Petal color upon maturity:

*Adaxial.*—Limb nearest RHS N78B with two bars about 0.5 mm long and 0.5 mm wide nearest RHS N78A and a central eye between the bars and corolla tube about 1.0 mm wide nearest RHS 76B; proximal 2.0 mm of tube nearest RHS 145C, remaining distal tube portion nearest RHS N75D.

*Abaxial*.—Limb nearest RHS 72B with area around inside eye nearest RHS 76D, proximal 2.0 mm of tube nearest RHS 145C, remaining distal tube portion nearest RHS N75B.

Androecium: Typically five;

*Filaments*.—Typically five, adnate to inner corolla to various heights about 6.0 mm to 10.0 mm from base; free in the distal 1.0 mm to 2.0 mm long and 0.2 mm in diameter; color nearest RHS NN155D.

*Anther*.—Five; oblong elliptic; basifixed; oblong, about 1.5 mm long by 0.7 mm wide; color nearest RHS 17B.

*Pollen*.—Nearly microscopic; color nearest RHS 23A.

Gynoecium: One pistil per flower; 9.0 mm long;

*Style*.—Cylindrical; about 6.5 mm long and 0.2 mm diameter when flower is mature; persistent after flower abscission; color nearest RHS 145D.

*Stigma*.—Trifid in proximal 1.5 mm long, about 0.2 mm diameter; color between RHS 4D and RHS 9B.

*Ovary*.—Inferior; conical; glabrous; lustrous; slightly acute apex and truncate base; about 1.0 mm long and 0.7 mm diameter; color nearest RHS 143A.

Calyx: Campanulate; pubescent abaxial, glabrous adaxial; about 10.0 mm long and 5.0 mm across at apex;

Sepals: Five; lanceolate; glabrous adaxial and puberulent abaxial; narrowly acute apex, fused in basal 4.0 mm; margin entire; matte abaxial, and lustrous adaxial; individually about 10.0 mm long and 1.0 mm wide at fusion;

Sepal color: Adaxial nearest RHS 138A with margin of nearest RHS 157C; abaxial nearest RHS 138A with strong blush in high light exposure to solid nearest RHS 187B;

Peduncle: Puberulent; strong, flexible; mostly upright; cylindrical; to about 1.5 mm diameter at base and 3.2 cm long; with average 3.3 flowers;

Peduncle color: Low light or ventrally nearest RHS 145B; high light or dorsally nearest RHS 146C with strong blush solid nearest RHS 187B;

Pedicle: Cylindrical; puberulent; flexible; upright to outwardly; variable lengths from about 9.0 mm to 6.0 mm long and 0.7 mm diameter;

Pedicle color: Variable depending on light exposure; with low light or ventrally nearest RHS 146D; high light or dorsally nearest RHS 187B;

Fruit and seeds: Not observed;

Hardiness and culture: The new plant grows best with full sun, light moisture and deep drainage; hardy to at least from USDA zone 4 through 8.

Disease and pest resistance: *Phlox* 'Ruby Riot' demonstrates excellent powdery mildew resistance under conditions that would normally show symptoms.

I claim:

1. A new and distinct cultivar of Hybrid Creeping *Phlox, Phlox* plant named 'Ruby Riot', as herein described and illustrated.

* * * * *